(12) United States Patent  (10) Patent No.: US 8,225,431 B2
Cyr  (45) Date of Patent: Jul. 24, 2012

(54) HEAD PROTECTIVE GEAR

(75) Inventor: Raymond Cyr, Laval (CA)

(73) Assignee: Eye Tactical Inc., Lachine (CA)

( * ) Notice: Subject to any disclaimer, the term of this patent is extended or adjusted under 35 U.S.C. 154(b) by 922 days.

(21) Appl. No.: 11/908,825

(22) PCT Filed: Mar. 17, 2006

(86) PCT No.: PCT/CA2006/000406
§ 371 (c)(1),
(2), (4) Date: Nov. 14, 2008

(87) PCT Pub. No.: WO2006/096992
PCT Pub. Date: Sep. 21, 2006

(65) Prior Publication Data
US 2009/0229043 A1  Sep. 17, 2009

Related U.S. Application Data

(60) Provisional application No. 60/662,371, filed on Mar. 17, 2005.

(51) Int. Cl.
*A42B 3/04* (2006.01)
(52) U.S. Cl. ............... 2/450; 2/6.3; 2/6.7; 2/15; 2/426; 2/429; 2/424
(58) Field of Classification Search ............... 2/455, 410, 2/6.2, 6.3, 6.6, 6.7, 422, 424, 425, 15, 10, 2/426, 427–429, 439, 448, 450, 452
See application file for complete search history.

(56) References Cited

U.S. PATENT DOCUMENTS

| | | | |
|---|---|---|---|
| 3,594,816 A | | 7/1971 | Webb et al. |
| 3,805,294 A | | 4/1974 | Rose et al. |
| 3,897,597 A | | 8/1975 | Kasper |
| 4,023,210 A | * | 5/1977 | Hanson ............................. 2/10 |
| 4,354,285 A | | 10/1982 | Rudd |
| 4,457,461 A | * | 7/1984 | Docking et al. .............. 224/181 |
| 4,556,995 A | * | 12/1985 | Yamamoto ....................... 2/439 |
| 4,922,550 A | | 5/1990 | Verona et al. |
| 4,987,608 A | | 1/1991 | Cobb |
| 5,012,528 A | | 5/1991 | Pernicka et al. |
| 5,265,276 A | | 11/1993 | Kimberly, Jr. |

(Continued)

FOREIGN PATENT DOCUMENTS
AU  2005200446 A1  8/2005

*Primary Examiner* — Christopher Harmon
(74) *Attorney, Agent, or Firm* — Goudreau Gage Dubuc; Hugh Mansfield

(57) ABSTRACT

There is disclosed a protective head gear comprising a helmet having a brim positioned above the eyes of the wearer, a face protector covering at least a portion of the face of the wearer, and an adapter comprising an elongate cross member for securing the face protector to the helmet along the brim. There is also disclosed an adapter for attaching a face protector having a pair of strap receiving slots molded therein to a helmet, comprising a cross member secured to the helmet, and a pair of support arms for insertion into the strap receiving slots. Additionally, there is disclosed face protective gear for use with a helmet having a brim positioned above the eyes of the wearer, comprising a cross member comprising a lip molded along an upper edge, and a pair of goggles depending from the cross member When the cross member is secured to the helmet, the lip overlaps the brim.

4 Claims, 5 Drawing Sheets

U.S. PATENT DOCUMENTS

| | | |
|---|---|---|
| 5,365,615 A | 11/1994 | Piszkin |
| 5,412,814 A | 5/1995 | Pernicka et al. |
| 5,666,663 A | 9/1997 | Bolle |
| 5,802,622 A * | 9/1998 | Baharad et al. ............. 2/434 |
| 5,987,652 A * | 11/1999 | Fowler ....................... 2/424 |
| 6,732,381 B1 * | 5/2004 | Lal ............................. 2/425 |
| 6,804,829 B2 * | 10/2004 | Crye et al. .................. 2/6.6 |
| 6,961,959 B2 | 11/2005 | Wang-Lee |
| 7,900,268 B2 * | 3/2011 | Mahan ........................ 2/6.5 |
| 2003/0070200 A1 * | 4/2003 | Crye et al. .................. 2/6.6 |
| 2005/0183190 A1 * | 8/2005 | Hussey ....................... 2/424 |
| 2005/0204446 A1 * | 9/2005 | Wright ........................ 2/9 |
| 2005/0241049 A1 * | 11/2005 | Ambuske et al. ........... 2/412 |
| 2008/0276933 A1 * | 11/2008 | Dampney et al. ...... 128/201.25 |

\* cited by examiner

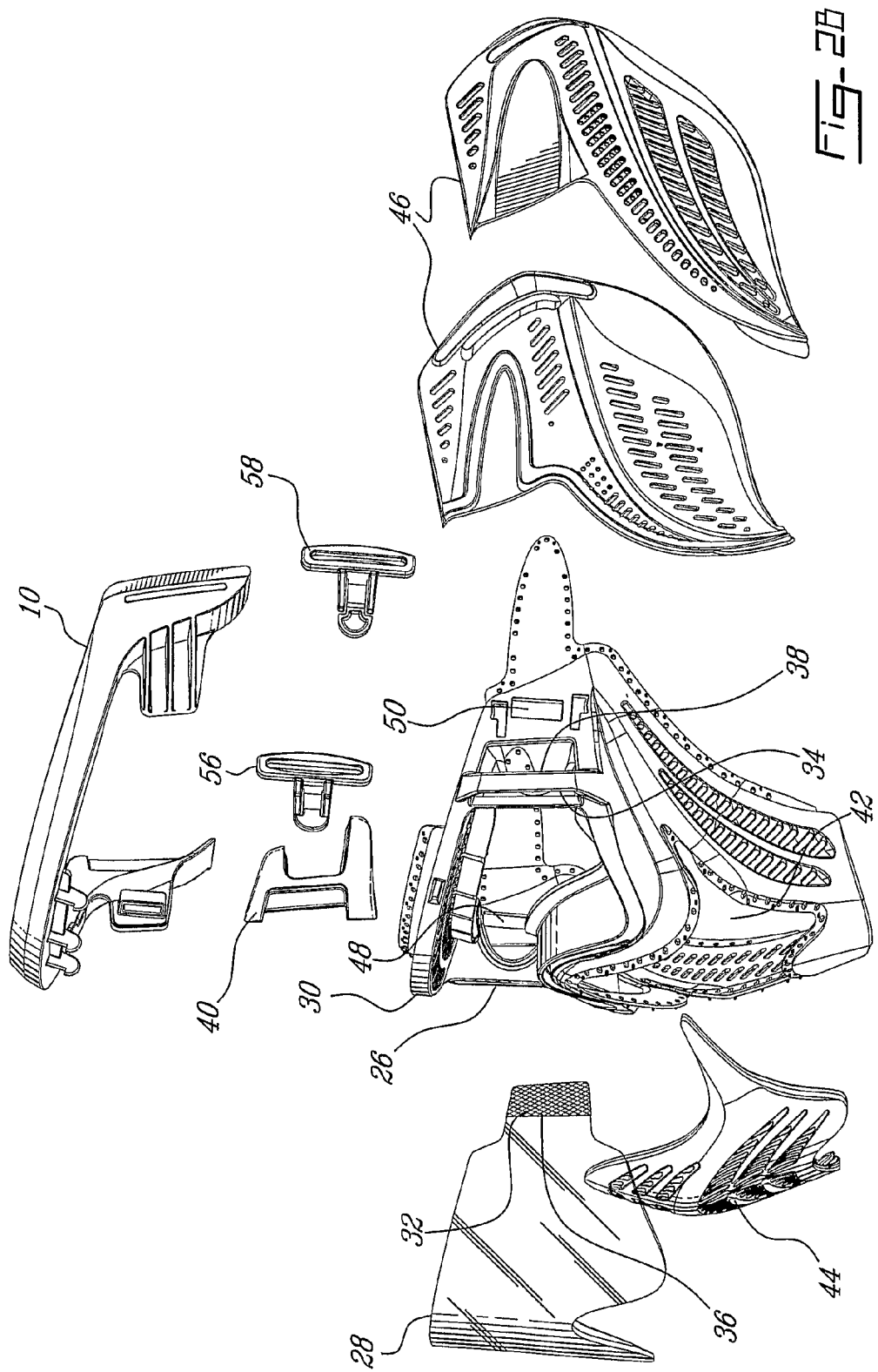

HEAD PROTECTIVE GEAR

CROSS-REFERENCE TO RELATED APPLICATIONS

This application is a National Entry Application of PCT application no PCT/CA2006/000406 filed on Mar. 17, 2006 and published in English under PCT Article 21(2), which itself claims priority on U.S. provisional application No. 60/662,371, filed on Mar. 17, 2005. All documents above are incorporated herein in their entirety by reference.

FIELD OF THE INVENTION

The present invention relates to a head protective gear. In particular, the present invention relates to an adapter for attaching a face protective gear to a helmet.

BACKGROUND OF THE INVENTION

Dangerous occupations, including many sports, require the participant to wear protective gear in order to ward off both minor and major injury. In many cases protective head gear as well as gear for protection of the eyes and face is an important aspect. As well known in the art, protective helmets are often combined with eye protection such as goggles or face masks in order to achieve these ends.

One drawback of such prior art approaches is that the goggles or face masks are first secured to the wearer's head using an elastic strap or the like, with the helmet then being placed on the wearers head over the strap. As a result, the elastic strap of the goggles sits underneath the helmet, which is uncomfortable. Alternatively, the strap can be placed over the helmet, but this in many cases leads to the outer edges of the goggles being raised off the wearer's face, thereby reducing the protection afforded by the goggles.

In order to address the above drawbacks, the prior art reveals visors which are integrated into the helmet. These visors typically improve the seal between eye and face protection and the helmet. However, they also exhibit a number of drawbacks. For example, they either enclose the wearer's face entirely (for example, in the case of a full face motorcycle helmet) or, in the case of partial visor, do not prevent material, projectiles and the like from entering from below the lower edge of the visor. Additionally, provision of a visor typically means that other protective goggles or facemasks cannot be worn, thereby limiting the versatility of the helmet.

The prior art also reveals adapters for improving attachment of the goggles by strap to the helmet, an example of which is disclosed in U.S. Pat. No. 5,666,663. One drawback of these prior art inventions is that although the goggles form a good seal with the wearer's face, the helmet and goggles are able to move relative to one another, and a gap where the wearer's face is exposed is typically formed between the upper edge of the goggles and the lower edge of the helmet. In activities where small high speed projectiles (such as bullets, BBs or Simunition®) are involved, such as warfare, paintball and simulated war games, exposure of the wearer in this manner can lead to significant injury and even death.

SUMMARY OF THE INVENTION

In order to address the above and other drawbacks, there is disclosed an adapter for attaching a face protector to a helmet, the face protector having a pair of strap receiving slots moulded therein. The adapter comprises a cross member secured to the helmet, and a pair of support arms, one of the support arms attached towards each end of the cross member, each of the support arms comprising a post adapted for insertion into one of the strap receiving slots.

There is also disclosed a protective gear to be worn on the head of a wearer. The protective gear comprises a helmet having a brim positioned above the eyes of the wearer, a face protector covering at least a portion of the face of the wearer, and an adapter comprising an elongate cross member for securing the face protector to the helmet along the brim.

Additionally, there is disclosed a face protective gear for use with a helmet worn by a wearer, the helmet having a brim positioned above the eyes of the wearer. The protective gear comprises a cross member comprising a lip moulded along an upper edge, and a pair of goggles depending from the cross member. When the cross member is secured to the helmet, the lip overlaps the brim.

BRIEF DESCRIPTION OF THE DRAWINGS

FIG. 2B is an exploded perspective view of the adapter and mask of FIG. 2A;

DETAILED DESCRIPTION OF THE ILLUSTRATIVE EMBODIMENTS

Figure 1:
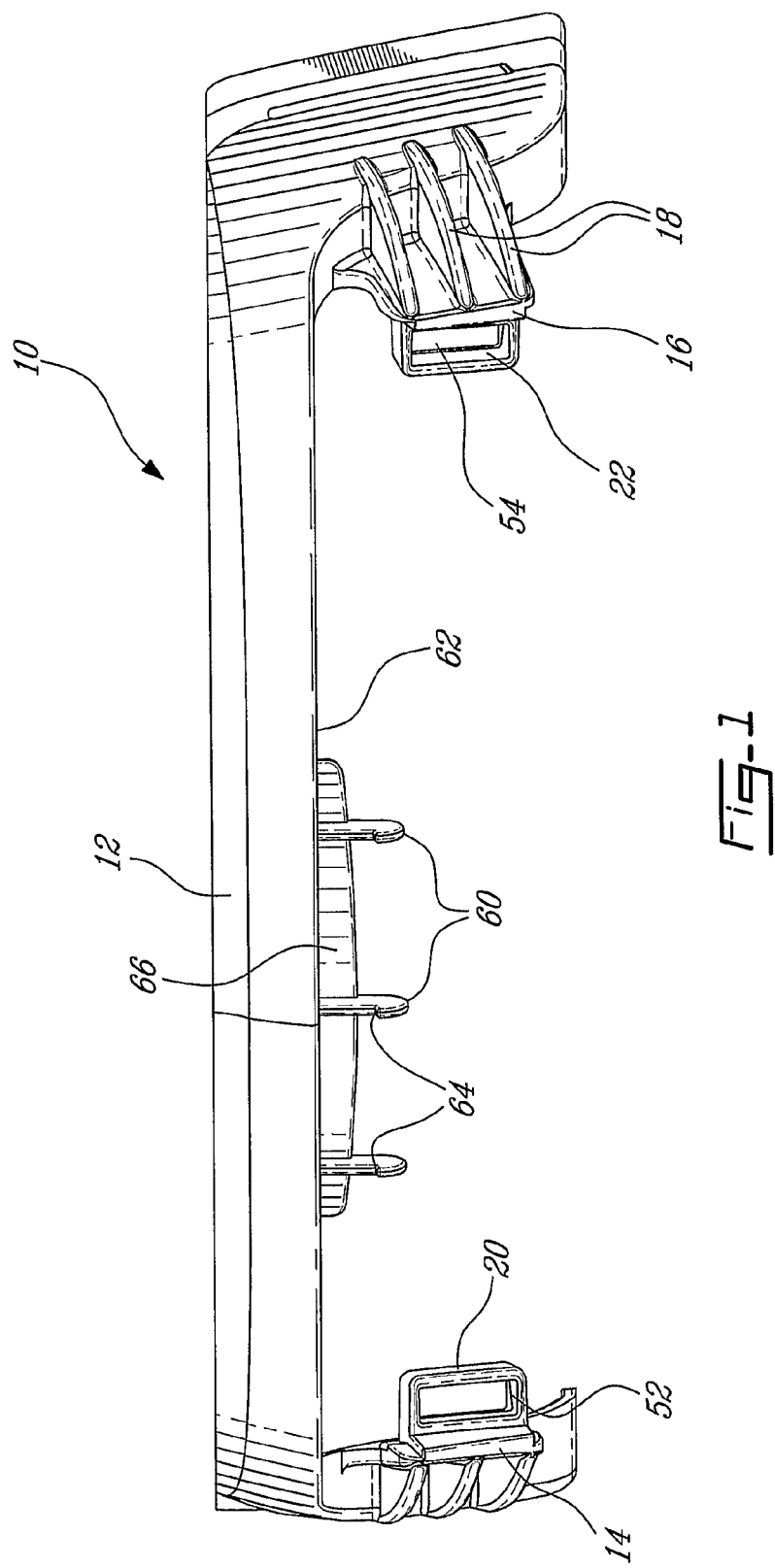
FIG. 1 is a right front perspective view of an adapter in accordance with an illustrative embodiment of the present invention.

Referring now to FIG. 1, a face protector (or mask) adapter generally referred to using the reference numeral 10 and in accordance with an illustrative embodiment of the present invention will now be described. The adapter 10 is comprised of a cross member 12 interconnecting a pair of support arms 14, 16. The support arms 14, 16 are provided with reinforcements as in 18 which help stabilise the support arms 14, 16. Each of the support arms further comprise a securing post as in 20, 22.

Figure 2A:
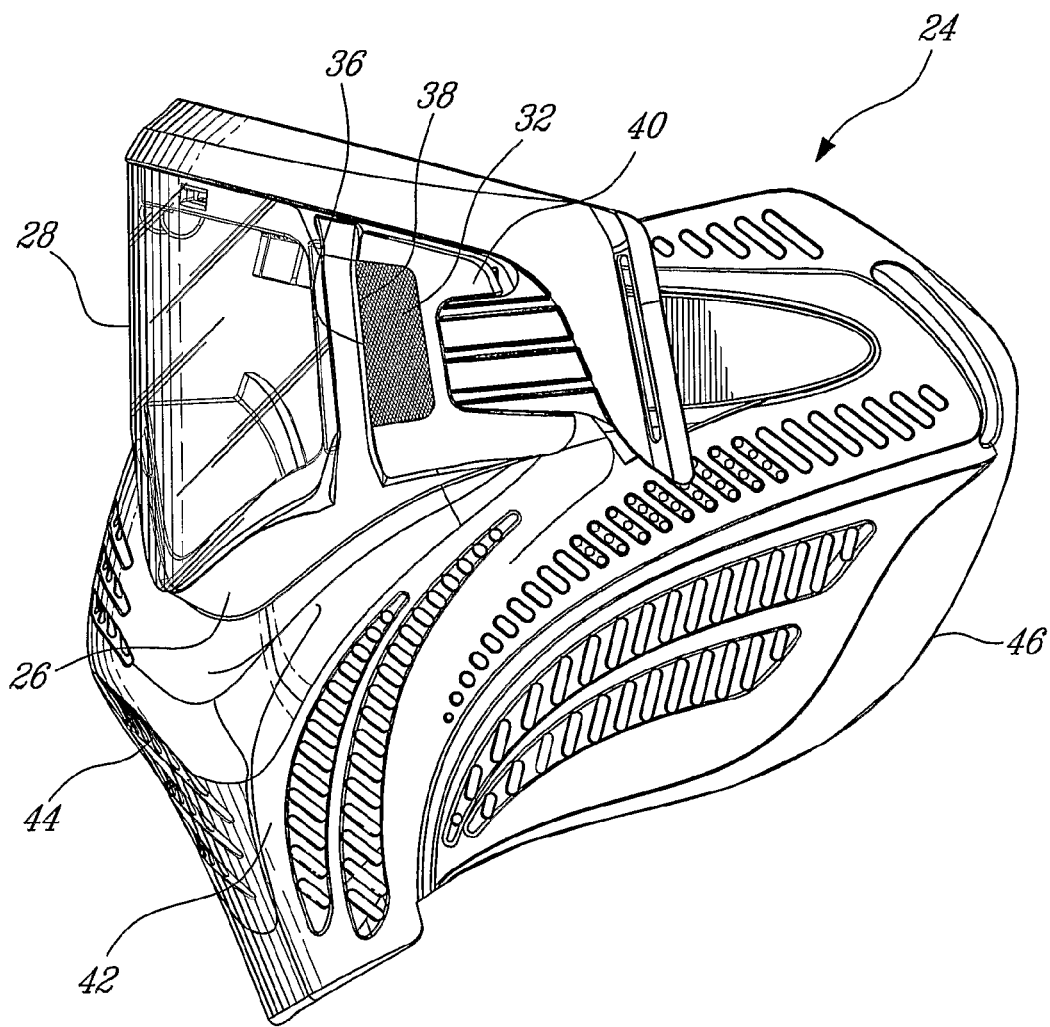
FIG. 2A is a side plan view of an adapter and mask in accordance with an illustrative embodiment of the present invention.

Referring now to FIGS. 2A and 2B, face protectors (or face protective gear) 24 are illustratively comprised of a pair of goggles 26 including a lens or lenses as in 28 (note that in some embodiments a plurality of tear-away lenses, not shown, are provided allowing a wearer to easily clear his vision if the outer lens becomes fouled with paint, dirt or the like). The lens 28 is illustratively held in place against the goggle frame 30 by inserting each tab end as in 32 of the lens 28 into a corresponding lens tab receiving slot as in 34 moulded in the goggle frame 30. Once inserted in its corresponding lens tab receiving slot as in 34, the inside edge 36 of the tab end 32 (which is raised somewhat above the surface of the lens 28), is engaged by the rearward facing edge 38 of the lens tab receiving slot as in 34. Additionally, once mounted to the goggle frame 30, each tab end 32 may be held more tightly in place using a lens retaining plate 40. Additionally a mouth protecting portion 42 is typically provided depending from the goggles 26 and thereby providing uninterrupted protection from the wearer's brow to chin. In order to facilitate assembly and other features the mouth protecting portion 42 may also include a removable mouth guard 44. Additional protective wings as in 46 may also be included for protecting the wearer's neck and ears.

As known in the art, goggles or face mask/protective gear as in 24 are typically secured to a wearer's face by means of one or more wide elastic straps (not shown) which typically circle the back of the wearer's head or helmet. Referring to FIG. 2B, such straps are typically attached to the mask 24 through provision of a pair of slots 48, 50, one of these slots 48, 50 being moulded in the mask 24 on either side of the lens 28.

Referring now to FIG. 1 in addition to FIG. 2B, the adapter 10 is mounted on the face mask 24 by removing the elastic strap from the mask 24 and inserting the securing posts as in 20, 22 into a complementary one of the slots as in 36. In order to ensure that the securing posts 20, 22 remain in the slots as in 36 each post as in 20, 22 is illustratively equipped with a hollow centre 52, 54. Once the securing posts 20, 22 have been inserted into the slots as in 36, a retainer (or retaining clip) as in 56, 58 is illustratively inserted through each of the hollow centres 52, 54.

Still referring to FIG. 1 and FIG. 2B, in order to further improve the union between mask 24 and adapter 10, a series of hook shaped fasteners as in 60 are arranged along the underside 62 of the cross member 12. When mounting the adapter 10 to the mask 24, the fasteners 60 are inserted into slots (not shown), for example air vents, moulded in the upper edge of the mask 24. The hook portion 64 of the fasteners 60 interlock with the mask 24, thereby preventing the cross member 12 from inadvertently being separated from the upper edge of the mask 24. Additionally, the fasteners 60 work in combination with a stabilising plate 66 to prevent the mask 24 from inadvertently moving laterally relative to the adapter 10.

Figure 3:
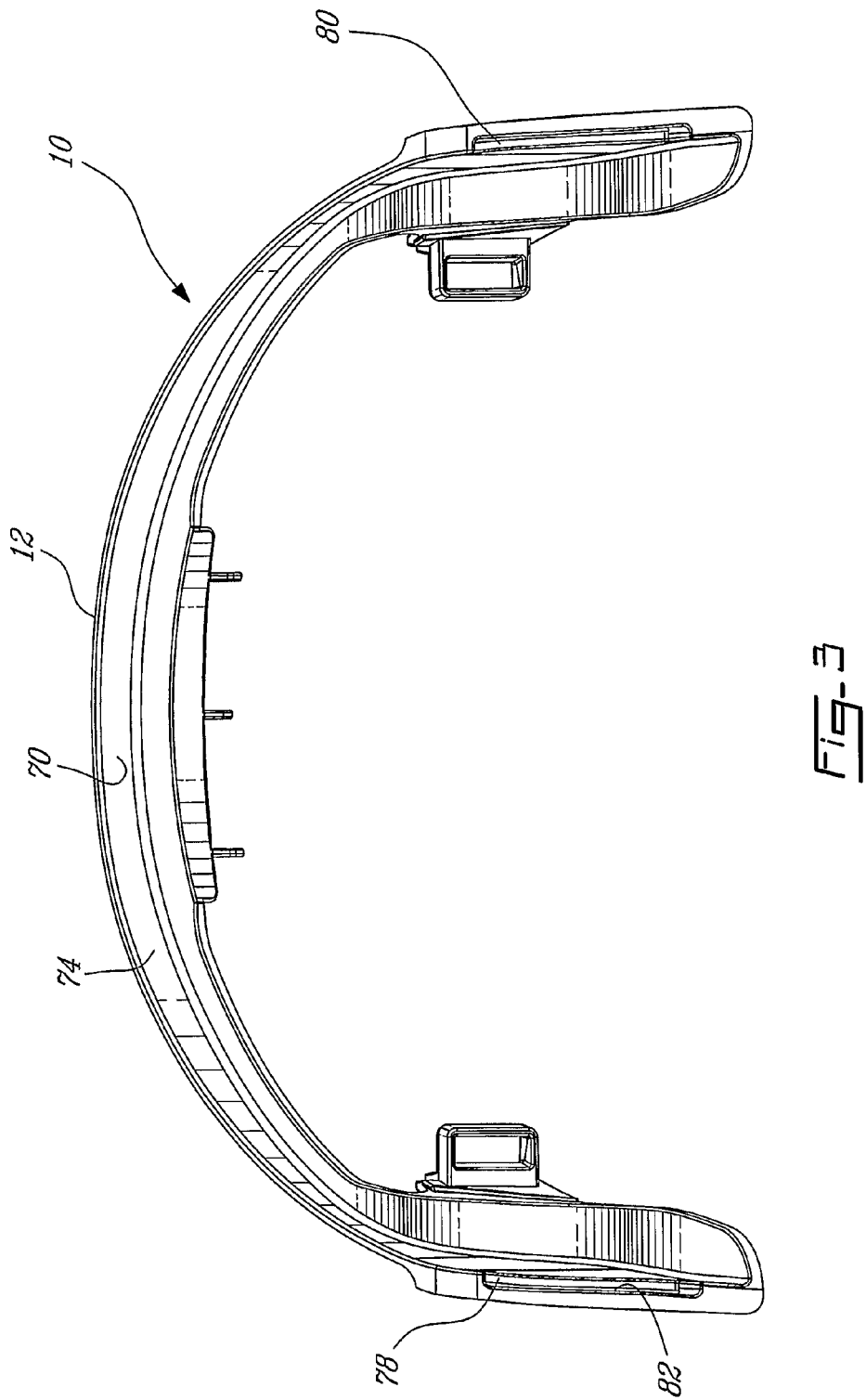
FIG. 3 is a rear perspective view of an adapter in accordance with an illustrative embodiment of the present invention.
Figure 4:
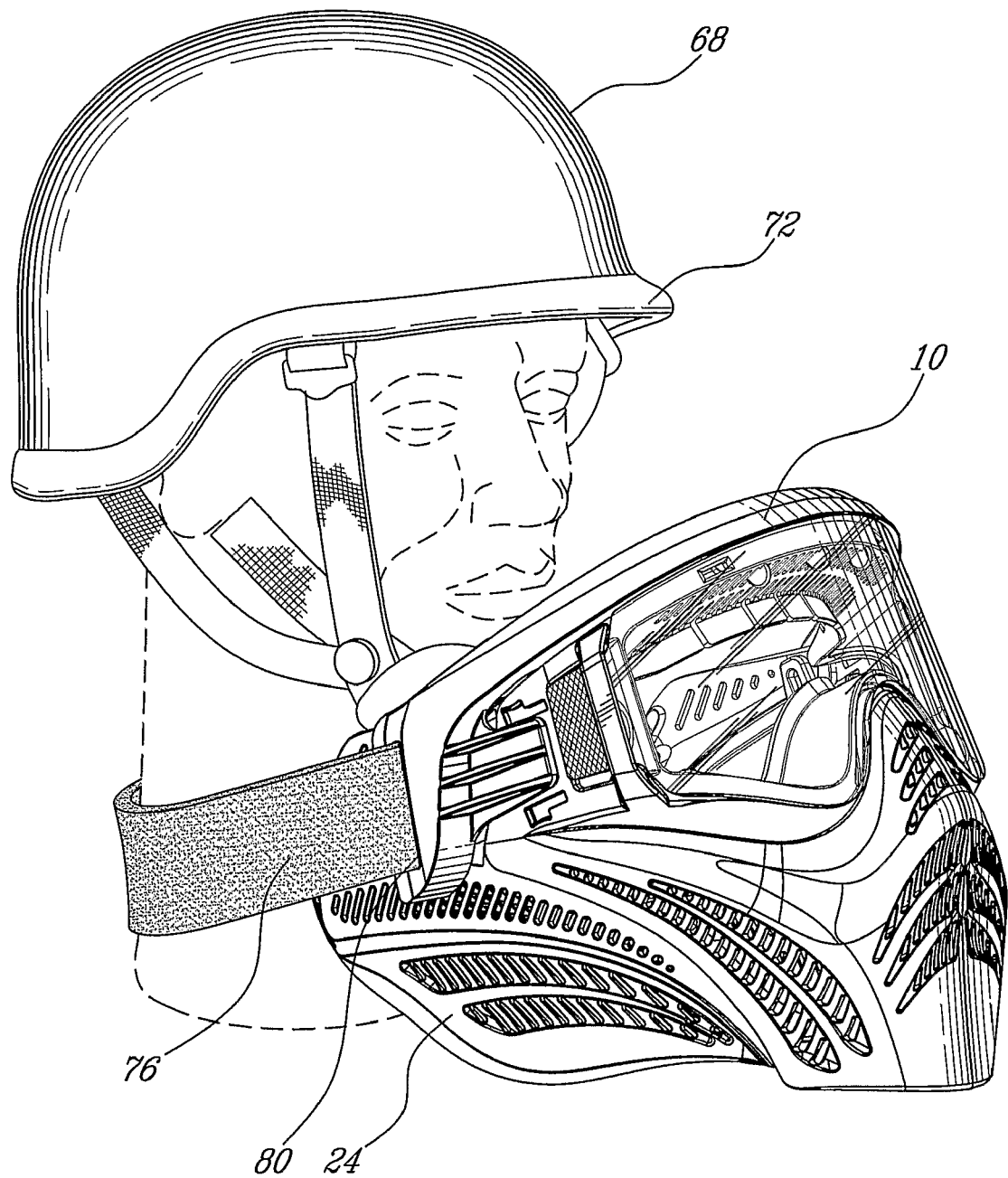
FIG. 4 is a left front perspective view of an adapter in accordance with an illustrative embodiment of the present invention attached to a mask and including a helmet.

Referring now to FIGS. 3 and 4, in order to mount the adapter 10 onto a helmet 68 or the like, the cross member 12 is curved and the inner surface 70 of the cross member 12 profiled to match the raised edge (or brim) 72 of the helmet 68. In this manner the cross member 12 comprises a lip 74 which overlaps with or extends above the raised edge (or brim) 72 of the helmet 68, thereby filling any gap which might otherwise be present between the face mask 24 and helmet 68.

The adapter 10 is secured to the helmet 68 through provision of an elastic strap 76 which is pulled around the helmet 68, thereby holding the adapter 10 and attached mask 24 securely in place. In order to improve the seal between the adapter 10 and helmet 68, the inner surface 70 can be coated with a suitable sealant (not shown), such as silicone rubber, prior to mounting on the raised edge (or brim) 72 of the helmet 68. Alternatively, a layer of elastic material (also not shown) such as foam rubber can be placed between the raised edge (or brim) 72 of the helmet 68 prior to mounting.

Still referring to FIGS. 3 and 4, in order to secure the elastic strap 76 to the adapter 10 a pair of strap receiving slots 78, 80 are provided in the adaptor 10. The strap receiving slots 78, 80 include cut away portions as in 82, provision of which allows the strap 76 to be mounted into the strap receiving slots 78, 80 flush with the inner surface 70, thereby improving the seal between adapter 10 and helmet 68. In an alternative embodiment, or in addition to the elastic strap 76, the adapter 10 can be mounted on the edge 72 of the helmet 68 using a suitable adhesive applied to the inner surface 70.

The adapter 10 is typically manufactured from a resilient durable material such as injection moulded plastic or composites such as Kevlar, but may also be manufactured completely or partially from a pliable material such as silicone rubber, Nylene™ or the like, in order to provide a better seal between the adapter, helmet and the wearer's face. Similarly, the goggles/mask 25 may be manufactured from injection moulded plastic or composites such as Kevlar or silicone rubber, Nylene™ or the like. Additionally, a combination of such materials may be used to provide a mask 24 which is both durable, comfortable to wear and able to withstand a projectile's impact. In a particular embodiment, the adapter 10 and mask 24 may be manufactured from a bullet proof material such as Kevlar.

It is to be understood that the invention is not limited in its application to the details of construction and parts illustrated in the accompanying drawings and described hereinabove. The invention is capable of other embodiments and of being practised in various ways. It is also to be understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

What is claimed is:

1. A protective gear to be worn on the head of a wearer, the protective gear comprising:
   a helmet having a brim positioned above the eyes of the wearer;
   a face protector covering at least a portion of the face of the wearer, said face protector comprising a first pair of strap receiving slots; and
   an adapter for securing said face protector to said helmet along said brim, said adaptor comprising an elongate cross member secured to said helmet and a pair of support arms, one of said support arms attached at each end of said cross member, and a pair of opposed posts each attached to a respective one of said support arms and depending inward, each of said posts inserted into a respective one of said first pair of strap receiving slots.

2. The protective gear of claim 1, wherein said face protector comprises a pair of goggles.

3. The protective gear of claim 1, wherein said elongate cross member has a brim receiving groove moulded along an upper edge therein.

4. The protective gear of claim 1, wherein said adapter further comprises an elastic strap for securing said cross member to said brim, said cross member further comprising a second pair of elastic strap receiving slots, each of said second pair of slots positioned towards an opposing end of said cross member and receiving an end of said elastic strap.

* * * * *